United States Patent
Seo et al.

(10) Patent No.: US 12,114,933 B2
(45) Date of Patent: Oct. 15, 2024

(54) SYSTEM AND METHOD FOR INTERVENTIONAL PROCEDURE USING MEDICAL IMAGES

(71) Applicant: Coreline Soft Co., Ltd., Seoul (KR)

(72) Inventors: Hyun Gi Seo, Goyang-si (KR); Donghoon Yu, Gimpo-si (KR); Jaeyoun Yi, Seoul (KR); Byeong Soo Kim, Bucheon-si (KR); Hyunwoo Kim, Seoul (KR); Ji Min Kim, Jeonju-si (KR)

(73) Assignee: Coreline Soft Co., Ltd., Seoul (KR)

( * ) Notice: Subject to any disclaimer, the term of this patent is extended or adjusted under 35 U.S.C. 154(b) by 859 days.

(21) Appl. No.: 17/139,361

(22) Filed: Dec. 31, 2020

(65) Prior Publication Data

US 2021/0196387 A1    Jul. 1, 2021

(30) Foreign Application Priority Data

Dec. 31, 2019   (KR) .......................... 10-2019-0179240

(51) Int. Cl.
*A61B 34/10*    (2016.01)
*A61B 34/00*    (2016.01)
*A61B 34/37*    (2016.01)

(52) U.S. Cl.
CPC .............. *A61B 34/10* (2016.02); *A61B 34/25* (2016.02); *A61B 34/37* (2016.02); *A61B 2034/107* (2016.02)

(58) Field of Classification Search
CPC ......... A61B 34/10; A61B 34/25; A61B 34/37; A61B 2034/107; A61B 2034/101;

(Continued)

(56) References Cited

U.S. PATENT DOCUMENTS 9,592,095 B2    3/2017   Panescu et al.
2011/0274324 A1*  11/2011   Clements ............... A61B 90/36
                                                    382/128

(Continued)

FOREIGN PATENT DOCUMENTS

JP    2008-18172 A    1/2008
KR    10-1464330 B1   11/2014

(Continued)

OTHER PUBLICATIONS

Gabor Fichtinger et al., "The Surgical CAD/CAM Paradigm and an Implementation for Robotically-Assisted Percutaneous Local Therapy," IEEE (2001) (Year: 2001).*

*Primary Examiner* — Steven W Crabb
(74) *Attorney, Agent, or Firm* — United One Law Group LLC; Kongsik Kim; Jhongwoo Peck

(57) ABSTRACT

Disclosed herein is a system for an interventional procedure using medical images. The system includes: a master device configured to perform control so that a medical tool of a robot arm follows intervention trajectories; an image processing device configured to register plan images, in which a surgical plan including the intervention trajectories of the medical tool is set up, and preoperative (pre-op) images acquired at a surgical site before surgery so that the surgical plan is transferred to the pre-op images and register the pre-op images and intraoperative (intra-op) images acquired at the surgical site during the surgery; and a user interface device configured to visualize the predicted arrival location of the tip of the medical tool for a target point when the robot arm operates according to the surgical plan by using the pre-op images and the intra-op images in conjunction with the image processing device.

7 Claims, 10 Drawing Sheets

(58) Field of Classification Search
CPC ... A61B 2034/252; A61B 34/20; A61B 10/02; A61B 34/32; A61B 90/37; A61B 2017/00119; A61B 2034/2065; A61B 2090/364; A61B 2090/3762; G06T 5/50; G06T 7/0012; G06T 7/11; G06T 2207/1008

See application file for complete search history.

(56) References Cited

U.S. PATENT DOCUMENTS

| | | | |
|---|---|---|---|
| 2015/0201892 A1 | 7/2015 | Hummel et al. | |
| 2017/0372474 A1* | 12/2017 | Behar | A61B 6/4441 |
| 2019/0231436 A1* | 8/2019 | Panse | A61B 34/30 |
| 2022/0361962 A1* | 11/2022 | Finley | A61B 34/20 |

FOREIGN PATENT DOCUMENTS

| | | |
|---|---|---|
| KR | 10-2016-0010539 A | 1/2016 |
| KR | 10-1758741 B1 | 8/2017 |
| KR | 10-1862133 B1 | 6/2018 |
| KR | 10-1954868 B1 | 3/2019 |

* cited by examiner

SYSTEM AND METHOD FOR INTERVENTIONAL PROCEDURE USING MEDICAL IMAGES

CROSS-REFERENCE TO RELATED APPLICATION

This application claims under 35 U.S.C. § 119(a) the benefit of Korean Patent Application No. 10-2019-0179240 filed on Dec. 31, 2019, which is incorporated herein by reference in its entirety.

TECHNICAL FIELD

The present invention relates to a system and method for an interventional procedure using medical images. More particularly, the present invention relates to the integrated workflow of the planning and procedure processes of a system and method for an interventional procedure, and also relates to a computing system that assists a system and method for an interventional procedure and software that is executed in the computing system.

The present invention was derived from the research conducted as part of the Robot Industry Core Technology R&D Project sponsored by the Korean Ministry of Trade, Industry and Energy and the Korea Evaluation Institute of Industrial Technology [Task Management Number: 1415162041; and Project Name: Development Of Commercialization Through Clinical Trials Of Interventional Procedure Robot System and Advancement Of Technology for Enhancement of Product Competitiveness].

BACKGROUND ART

A medical image-based biopsy is an interventional procedure that extracts samples required for the pathological diagnosis of an abnormal lesion while minimizing damage to surrounding normal tissues. It is widely applied to various organs in the retroperitoneum or abdominal cavity such as the adrenal glands, the pancreas, and the lymph nodes and various regions such as the lungs, the mediastinum, the spine, and the extremities. In a medical image-based biopsy, a lesion region is delicately localized in three dimensions using high-resolution images and a biopsy needle having entered tissue can be viewed, so that it is easy to detect a lesion having a small size.

At a treatment site where a medical image-based biopsy is performed, a biopsy needle can be guided through intervention trajectories by using a computed tomography (CT) scanner or C-arm fluoroscopy device and images therefrom. For example, when intervention trajectories are planned, the intervention trajectories of a biopsy needle can be accurately planned by determining the entry angle and insertion point of the biopsy needle in the body of a patient. When the patient enters the treatment site and then surgery begins, an image acquisition device (e.g., a fluoroscopy device or CBCT device) placed at the treatment site is oriented along the planned trajectories, i.e., the orientation in which the biopsy needle will be inserted.

In the biopsy process, a navigation view is used to accurately guide the biopsy needle. For example, in a navigation view such as a Surgeon's Eye View, when the entry point is pierced with the biopsy needle, the center point of a target is seen and the biopsy needle appears as a point based on the insertion point. In this navigation view, the target is shown as a point, and a circle is drawn around the point. In this case, it can be possible to plan the distance and angle over and at which the biopsy needle is struck based on the plan for the intervention trajectories.

However, recently, it is widely accepted that a tumor is not homogeneous and the biological properties (e.g., DNA mutation, and malignancy) of the tumor differ (heterogeneous) according to each portion of the tumor. The region where tissue was collected is an important issue in tumor diagnosis, tumor treatment effect prediction, and patient prognosis estimation. For example, there is a case where an active cancer cell is located at the edge of a tumor and the inside of the tumor is necrotic so that there is no tumor cell inside the tumor. Accordingly, when a biopsy needle is stuck into the center of a tumor, an error of false-negative diagnosis may occur. Therefore, in order to biopsy a tumor having such heterogeneity, a surgeon may intentionally pierce the outer edge of the tumor based on his or her experience while viewing a fluoroscopy image. However, it is not easy for the surgeon to pierce the center of the tumor as planned. It can be technically very difficult to accurately biopsy tumor cells distributed at the edge of a relatively highly difficult tumor.

Furthermore, it is very important from a medical point of view to biopsy a heterogeneous tumor using a multi-spot method that performs biopsy at multiple target points and construct a map representing the properties of tissue according to the location in the tumor by matching biopsy locations and the characteristics of samples. It is more difficult for a surgeon to perform a biopsy using the multi-spot method based on his or her experience.

As an attempt to improve the convenience of an interventional procedure using medical images, Korean Patent No. 10-1758741 entitled "Guidance Method for Interventional Procedure using Medical Images and System for Interventional Procedure for the Same" was introduced. An attempt to improve a surgical tool and a workflow by reflecting the diversity and heterogeneity of targets was introduced in Korean Patent No. 10-18621333 entitled "Needle Insertion-Type Interventional Procedure Robot Apparatus."

Meanwhile, preoperative (pre-op) images acquired at a surgery site have lower resolution than plan images acquired in advance, and intraoperative (intra-op) images (or fluoroscopy images) acquired in real time have lower resolution in order to reduce the risk of exposure to radiation. It is difficult to secure high accuracy within a limited time because image registration and association must be performed rapidly despite the low resolution.

Korean Patent No. 10-1954868 entitled "Navigation System for Vascular Interventional Procedure and Virtual X-ray Image Generation Method" introduces a configuration in which a local model of a three-dimensional image is generated and the local model is registered into real X-ray images taken during the interventional procedure of a patient. Although an attempt is made to increase the accuracy of mapping in a 3D space for inter-image association within a limited time by rapidly perform registration using a local model, there is still a problem in that accuracy is poor when high-resolution images at a planning stage are associated with low-resolution images acquired at an actual surgical site.

As an attempt to rapidly perform image registration and classification, Korean Patent No. 10-1464330 entitled "Method of Comparing Pre-op Breathing Level and Intra-op Breathing Level" introduces a configuration that compares a pre-op breathing level and an intra-op breathing level by using a pre-op image template and an intra-op image template.

However, the prior art uses image templates, and thus it is not easy to deal with the diversity and heterogeneity of targets at actual sites.

SUMMARY OF THE DISCLOSURE

In order to rapidly and accurately register and associate plan images, pre-op images, and intra-OP images (or fluoroscopy images) within a limited time at an interventional procedure site, an improved workflow is required.

There has been a demand for an integrated workflow which can respond to the diversity and heterogeneity of targets at actual sites while being rapid and accurate and to which an image processing technique, robust to environments such as the resolution of images acquired at surgical sites, is applied.

The present invention has been conceived to overcome the above-described problems of the prior art, and an object of the present invention is to propose a system for an interventional procedure, which may provide the workflow of planning and procedure processes via integrated software and an integrated computing system and may also propose a guidance method for an interventional procedure that is performed in the system for an interventional procedure.

In the case of performing registration using only a local model as in Korean Patent No. 10-1954868 entitled "Navigation System for Vascular Interventional Procedure and Virtual X-ray Image Generation Method" among the prior art, it is not possible to accurately identify and detect a case where a surgical tool at a surgical site invades an organ or deviates from trajectories, so that such accidents cannot be prevented in advance. Accordingly, information about surrounding anatomical structures as well as the local model needs to be utilized.

An object of the present invention is to propose a system and method for an interventional procedure using corresponding medical images, which may utilize the anatomical structure information of pre-op images having the highest similarity to the anatomical structures in intra-op images and deal with association with insufficient information and surgical plan data attributable to low resolution by means of registration and association with plan images having high resolution.

An object of the present invention is to propose a system and method for an interventional procedure using medical images, which may obtain accurate information about the relationship between anatomical structures in intra-op images and the current location and direction of a surgical tool based on high resolution when a surgical plan and plan images are present.

An object of the present invention is to propose a system and method for an interventional procedure using medical images, which, even when a surgical plan and plan images are not present, may utilizes the anatomical structure information of pre-op images, obtain accurate information about the relationship between anatomical structures in intra-op images and the current location and direction of a surgical tool based on high resolution, and improve the safety of an interventional procedure.

An object of the present invention is to propose a system and method for an interventional procedure using medical images, which may determine the location and direction of a surgical tool in a three-dimensional (3D) anatomical space by using pre-op images in a pre-op planning stage or at a surgery site and intra-op images during surgery, so that the system and method for an interventional procedure do not require or may minimize additional location trackers, sensors attached to a patient, and/or a navigation system.

According to an aspect of the present invention, there is provided a system for an interventional procedure using medical images, the system including: a robot base located beside a patient table supporting a patient, and configured to be movable; a robot arm provided with a medical tool, and configured to operate such that the medical tool follows intervention trajectories; a master device configured to perform control so that the medical tool of the robot arm follows the intervention trajectories; an image processing device configured to register plan images, in which a surgical plan including the intervention trajectories of the medical tool is set up, and preoperative (pre-op) images acquired at a surgical site before surgery so that the surgical plan is transferred to the pre-op images and register the pre-op images and intraoperative (intra-op) images acquired at the surgical site during the surgery; and a user interface device configured to visualize the predicted arrival location of the tip of the medical tool for a target point when the robot arm operates according to the surgical plan by using the pre-op images, to which the surgical plan has been transferred, and the intra-op images in conjunction with the image processing device. The image processing device is further configured to distinguish first and second areas in the pre-op images, identify second anatomical structures by performing image segmentation on the first area, and register third anatomical structures in the second area and first anatomical structures corresponding to the third anatomical structures in the plan images for the second area.

The image processing device may be further configured to distinguish the first and second areas in the pre-op images based on their correlations with the surgical plan.

The image processing device may be further configured to distinguish the first and second areas in the pre-op images based on the characteristics of the second and third anatomical structures in the pre-op images.

The image processing device may be further configured to segment the first anatomical structures in the plan images and map the intervention trajectories, included in the surgical plan, to the first anatomical structures.

The image processing device may be further configured to register the pre-op images and the intra-op images, thereby comparing a current location and direction of the surgical tool in the intra-op images with the intervention trajectories on the surgical plan identified in the pre-op images and determining whether the surgical tool in the intra-op images invades anatomical structures identified in the pre-op images.

According to another aspect of the present invention, there is provided a system for an interventional procedure using medical images, the system including: a robot base located beside a patient table supporting a patient, and configured to be movable; a robot arm provided with a medical tool, and configured to operate such that the medical tool follows intervention trajectories; a master device configured to set up the medical tool of the robot arm and perform control so that the medical tool of the robot arm follows the intervention trajectories; an image processing device configured to register preoperative (pre-op) images acquired at a surgical site before surgery and intraoperative (intra-op) images acquired at the surgical site during the surgery; and a user interface device configured to visualize the predicted arrival location of the tip of the medical tool for a target point when the robot arm operates according to the intervention trajectories by using the intra-op images in conjunction with the image processing device. The image processing device is further configured to identify fourth anatomical structures in the pre-op images by performing image segmentation on the pre-op images, and register fifth anatomical structures identified in the intra-op images and the fourth anatomical structures in the pre-op images.

The image processing device may be further configured to register the pre-op images and the intra-op images, thereby determining whether the surgical tool in the intra-op images invades anatomical structures identified in the pre-op images based on the current location and direction of the surgical tool in the intra-op images.

According to still another aspect of the present invention, there is provided a method for an interventional procedure using medical images, which is performed by a computing system. The method includes: acquiring or receiving plan images for a patient; performing image segmentation on the plan images, and identifying first anatomical structures in the plan images; setting up a surgical plan, including the intervention trajectories of a surgical tool, based on the plan images; mapping the surgical plan to the first anatomical structures, and storing the surgical plan mapped to the first anatomical structures; loading the stored surgical plan; acquiring or receiving pre-op images acquired at a surgical site before surgery; transferring the surgical plan to the pre-op images by registering the plan images and the pre-op images; acquiring or receiving intra-op images acquired at the surgical site during the surgery; and mapping the current location and trajectory of the surgical tool, identified in the intra-op images, to anatomical structures in the pre-op images by registering the pre-op images and the intra-op images.

The transferring may include distinguishing first and second areas in the pre-op images, identifying second anatomical structures by performing image segmentation on the first area, and registering the first anatomical structures in the plan images and third anatomical structures in the second area corresponding to the first anatomical structures for the second area.

According to still another aspect of the present invention, there is provided a method for an interventional procedure using medical images, which is performed by a computing system. The method includes: acquiring or receiving preoperative (pre-op) images acquired at a surgical site before surgery; acquiring or receiving intraoperative (intra-op) images acquired at the surgical site during the surgery; registering the pre-op images and the intra-op images; and mapping a current location and trajectory of the surgical tool, identified in the intra-op images, to anatomical structures in the pre-op images. The registering may include identifying fourth anatomical structures in the pre-op images by performing image segmentation on the pre-op images and registering fifth anatomical structures identified in the intra-op images and the fourth anatomical structures in the pre-op images.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE DISCLOSURE

Other objects and features of the present invention in addition to the above-described objects will be apparent from the following description of embodiments taken with reference to the accompanying drawings.

Embodiments of the present invention will be described in detail below with reference to the accompanying drawings. In the following description, when it is determined that a detailed description of a related known component or function may unnecessarily make the gist of the present invention obscure, it will be omitted.

As a known technology in the art to which the present invention pertains, specific details of the workflow of an interventional procedure guided by medical images and/or an automated robotic system for performing an interventional procedure are disclosed in the above-described Korean Patent No. 10-1758741 entitled "Guidance Method for Interventional Procedure using Medical Images and System for Interventional Procedure for the Same" and the above-described Korean Patent No. 10-18621333 entitled "Needle Insertion-Type Interventional Procedure Robot Apparatus." These well-known hardware, software, and workflows may be combined with some of the components of the present invention for the purpose of the specific implementation of the present invention.

Figure 1:
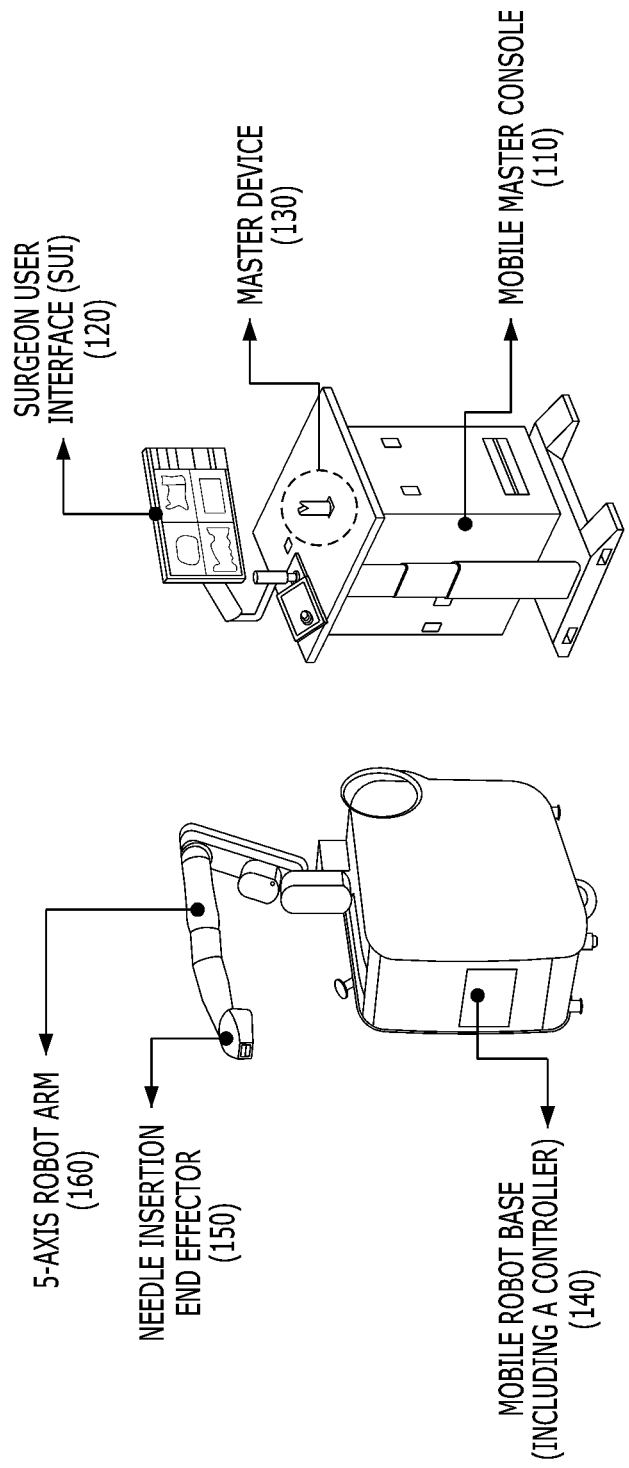
FIG. 1 is a view showing an overview of a system for an interventional procedure using medical images according to an embodiment of the present invention.

FIG. 1 is a view showing an overview of a system for an interventional procedure using medical images according to an embodiment of the present invention. The system for an interventional procedure is an automated system robot surgery apparatus that is connected to an image acquisition device such as CT scanner for the purpose of biopsy, ablation, or anesthesia, shows acquired images to a user, guides an actual procedure tool through a desired location and direction after the user has directly designated the insertion location and depth of a puncture needle, a biopsy needle, or an ablator, and inserts the needle into the human body and adjusts intervention trajectories by controlling the needle using a master device and a master console.

Referring to FIG. 1, the system for an interventional procedure using medical images includes: a robot arm 160 having one or more joints; a master device 130 and mobile master console 110 configured to set up a procedure plan based on pre-procedure images or control the robot arm 160 in real time; and a surgeon user interface (SUI) 120 configured to monitor and display the movement of a needle insertion end effector 150 attached to the robot arm 160, the location and posture of a patient, and the like and allow a user who is a medical professional to perform surgery.

The robot arm 160 may be a part of a slave robot, and the end effector 150 may be mounted at an end of the robot arm 160. A medical tool may be mounted on the end effector 150, and for the purpose of automating a procedure, the end effector 150 may drive the medical tool by directly transmitting power to the medical tool. The medical tool may be interchangeable, and may have a combined structure such that a plurality of medical tools is mounted on a single end effector and used simultaneously in a single procedure. The medical tool may include a micro-sensor. The master console 110, which is a computing system, may be provided with a communication module to enable the transmission of information.

The medical tool may be a medical device such as a biopsy needle, a lead (e.g., a lead for deep brain stimulation), a probe, or a catheter. It is obvious that the medical tool mounted on the robot arm 160 is not limited thereto. In this example, a biopsy needle is mainly described as an example below. The biopsy needle may be composed of a needle for tissue collection (e.g., an inner stylet; see FIG. 1), and a guide needle (e.g., a sheath) for guiding the needle for tissue collection, or may be composed of only a guide needle.

A CT scanner, a C-arm fluoroscopy device, or the like may be used as an image acquisition device (not shown) at a surgical site. For example, a table moves a patient into and out of a CT scanner. The robot arm 160 is mounted and moved on a robot base 140 movable beside the table, and a part of the robot arm 160 may enter or exit the CT scanner.

The master console 110 operates in conjunction with the CT scanner and the robot arm 160, and operates in conjunction with an image processing device that performs real-time image registration. The image processing device may be implemented as a separate computing system, or may be included in the master console 110. When the image processing device is included in the master console 110, real-time image registration may be implemented by image processing software that is executed in the master console 110.

The master device 130 may include an interface that receives user inputs and control commands. Sensory haptics is applied to the master device 130 so that when a biopsy needle is inserted into a target and meets an obstacle or when it is necessary to give a signal indicating a specific point, a vibration response for the force that the obstacle exerts on the biopsy needle or a signal for the specific point may be provided to the master device 130. In addition, this may be utilized for the training of an interventional procedure. In an embodiment of the present invention, when the current position and direction of the biopsy needle deviate from a surgical plan or recommended intervention trajectories, invades another organ, or is expected to do so, a vibration response may also be provided to the master device 130 as an alarm.

The SUI 120 displays a surgical plan, real-time intra-op images, and pre-op images, and also displays the current location and direction of the biopsy needle, thereby safely and accurately guiding the interventional procedure and improving the convenience of the interventional procedure.

When a surgical plan is set up and then an interventional procedure is performed according to the surgical plan, the robot arm 160 operates such that the medical tool attached to the end effector 150 follows intervention trajectories. The master device 130 may guide the medical tool to follow the intervention trajectories included in the surgery plan, and may guide the medical tool so as not to deviate from the intervention trajectories when a user controls the medical tool by operating the master device 130.

The SUI 120 may visualize a target point or the predicted arrival location of the tip of the medical tool for a procedure target region when the robot arm 160 is operating, and may display the current position and direction of the moving medical tool in real time.

The software of the system for an interventional procedure is divided into planning software and procedure software. The planning software is software that supports the process of setting up an interventional procedure plan based on CT images, and the procedure software is software that assists in reading a procedure plan from a robot system and performing a procedure using it.

The workflow of the operation of a robot for an interventional procedure according to the present invention is supported by integrated software for an interventional procedure into which planning software and procedure software are integrated, and main functions executed in each piece of software will be described below.

Figure 2:
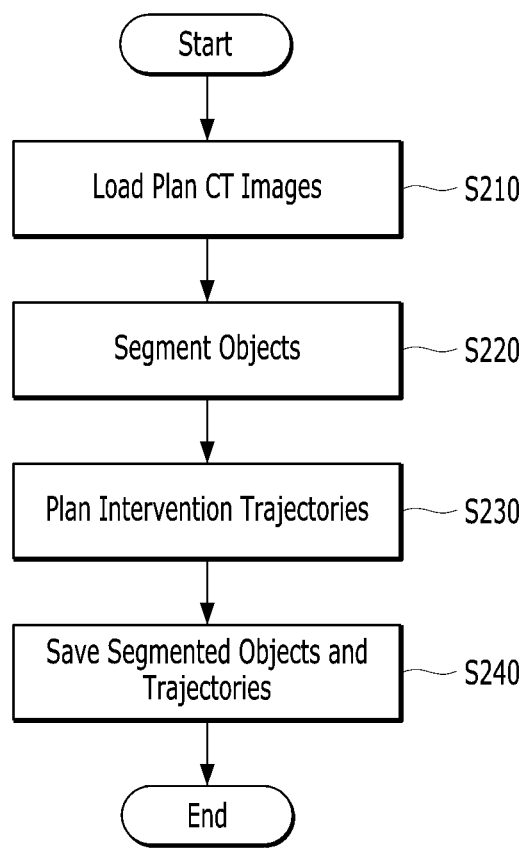
FIG. 2 is an operational flowchart showing the planning process of a method for an interventional procedure according to an embodiment of the present invention that is performed in the system for an interventional procedure shown in FIG. 1.

FIG. 2 is an operational flowchart showing the planning process of a method for an interventional procedure according to an embodiment of the present invention that is performed in the system for an interventional procedure shown in FIG. 1.

The steps of FIG. 2 are supported by a planning software part, and may be loaded and executed by a processor of a computing system located inside the mobile master console 110 or connected to the mobile master console 110. In particular, steps S220 and S230 may be performed by an image processing apparatus of a computing system located inside the mobile master console 110 or connected to the mobile master console 110.

Referring to FIG. 2, plan CT images may be acquired by being connected to a CT scanner or may be received by the planning software at step S210.

At step S220, objects, more specifically first anatomical structures, in the plan CT images may be segmented by the planning software. The first anatomical structures refer to the lungs, the airways, the pulmonary blood vessels, the bones, the skins, and the like included in the plan CT images. In this case, a procedure target area may also be segmented from surrounding organs as a separate anatomical structure.

In a state in which the planning software is executed, the plan CT images are displayed on the SUI 120. In this case, the first anatomical structures segmented by step S220 may be displayed on the SUI 120.

Figure 3:
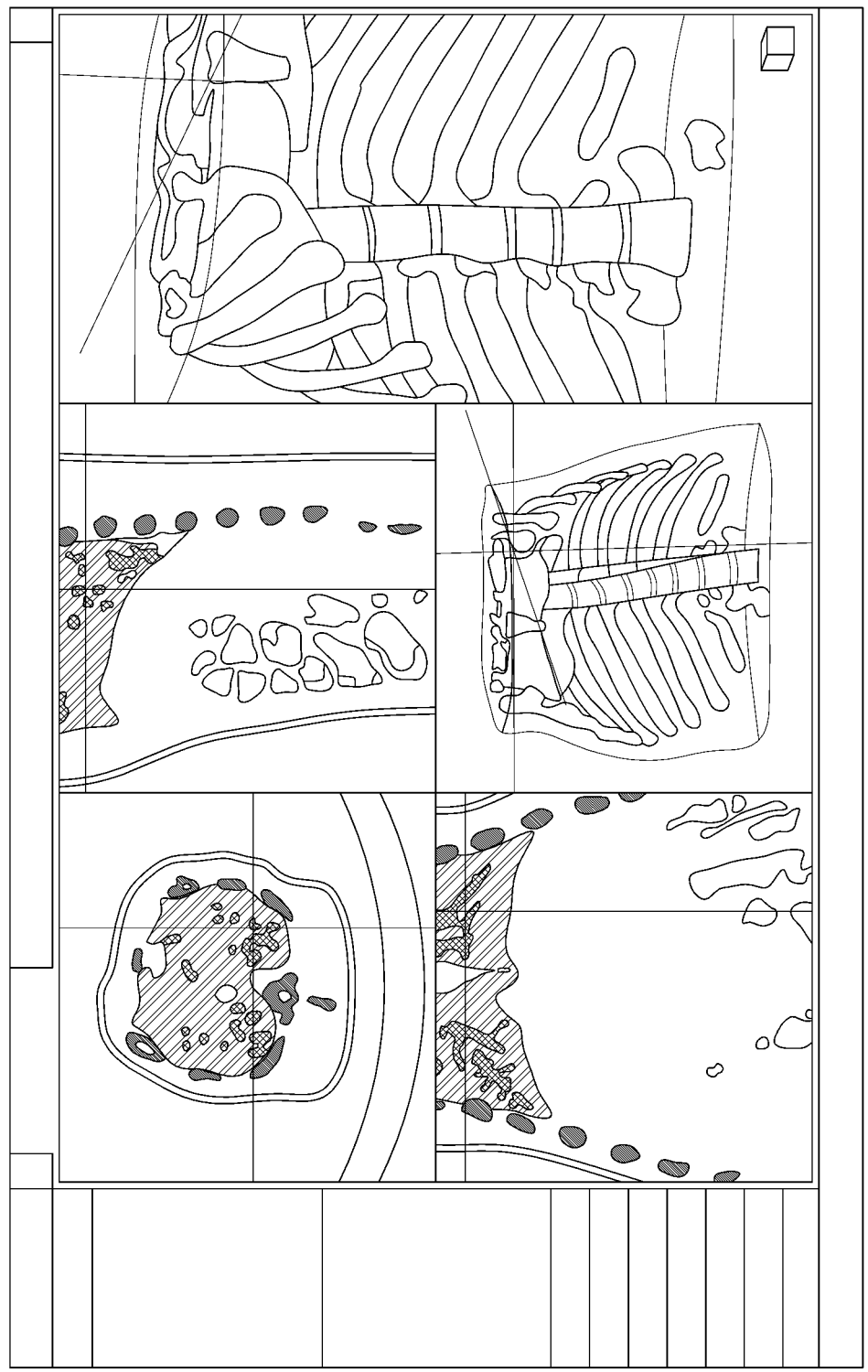
FIG. 3 is a view showing an example of the step of segmenting plan images in the planning process of the method for an interventional procedure shown in FIG. 2.

FIG. 3 is a view showing an example of step S220 of segmenting plan images in the planning process of the method for an interventional procedure shown in FIG. 2.

Referring to FIG. 3, the results of the segmentation of bones and other organs are displayed in different colors.

Referring back to FIG. 2, in a state in which the planning software is executed and the first anatomical structures segmented by step S220 are displayed on the SUI 120, a user may plan intervention trajectories included in the surgical plan by operating the master device 130. In this case, the planning software may automatically support the overall step of planning intervention trajectories or semi-automatically support a part of the step of planning intervention trajectories at step S230.

Figure 4:
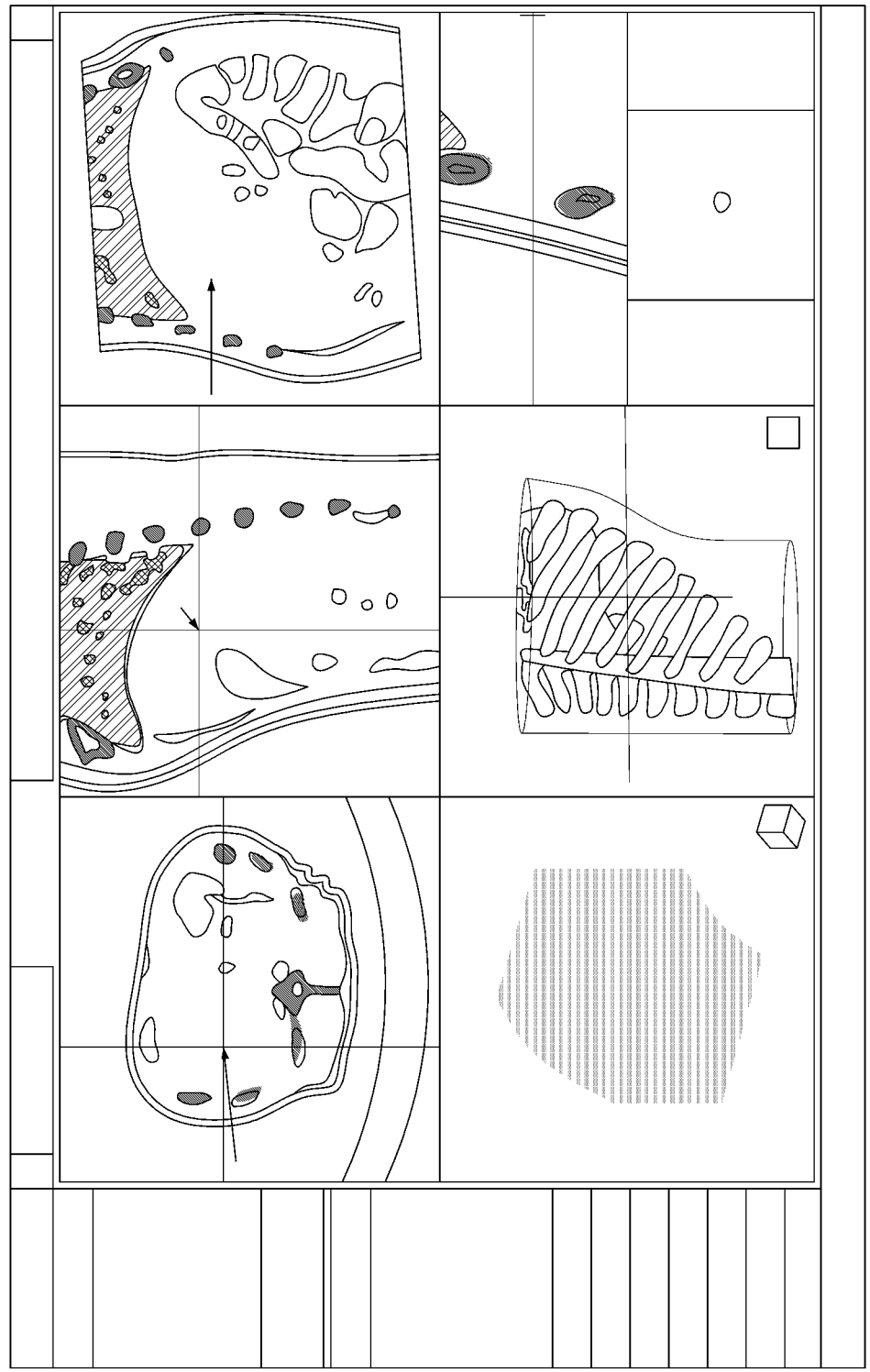
FIG. 4 is a view showing an example of the step of planning intervention trajectories in the planning process of the method for an interventional procedure shown in FIG. 2.

FIG. 4 is a view showing an example of step S230 of planning intervention trajectories in the planning process of the method for an interventional procedure shown in FIG. 2.

Referring to FIG. 4, a procedure target area, which is the final target of the surgical plan, and intervention trajectories, which are paths to the procedure target area, are displayed using visual elements (colors, patterns, and/or symbols) that are distinguished from other anatomical structures.

In this case, the image processing device located inside the mobile master console 110 or connected to the mobile master console 110 may map the intervention trajectories, included in the surgical plan, to the segmented first anatomical structures in the plan CT images, and may display the intervention trajectories mapped to the segmented first anatomical structures to the user via the SUI 120.

Referring back to FIG. 2, in a state in which the planning software is being executed, the planning software may store the segmented objects (the first anatomical structures) and the intervention trajectories mapped thereto in response to the operation of a user at step S240.

In general, the plan CT images, which are the basis for setting up the surgical plan, are taken using the highest dose in the workflow of an interventional procedure, and have the highest resolution. Additionally, the image segmentation of the anatomical structures in the plan images may be performed for a sufficiently long time because there is little time constraint. Accordingly, the anatomical structures in the plan images may be most easily segmented, and the surgical plan and the intervention trajectories may be mapped to and stored in association with the detailed segmented anatomical structures.

Figure 5:
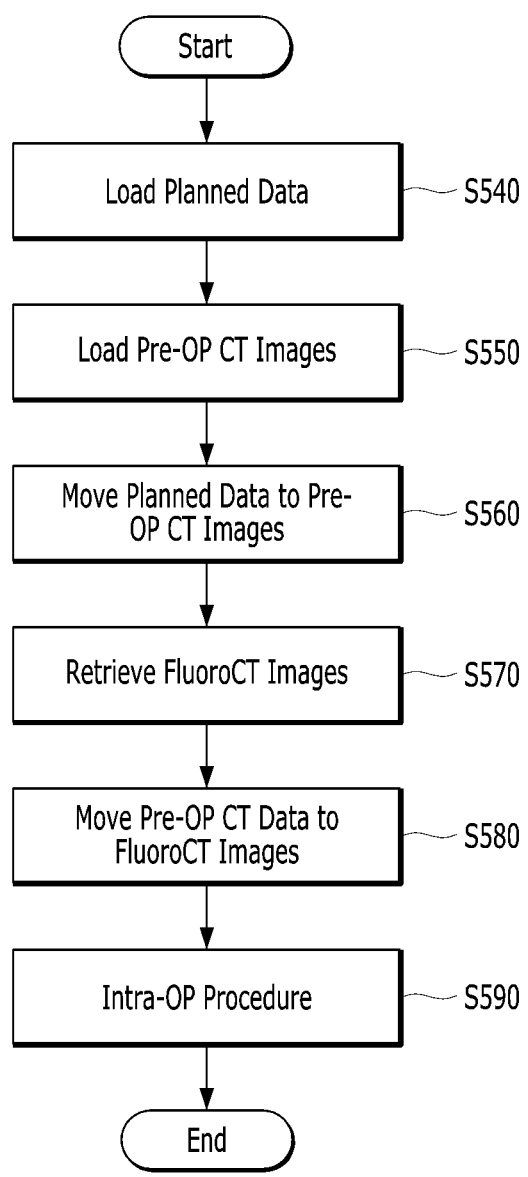
FIG. 5 is an operational flowchart showing the procedure process of the method for an interventional procedure according to the embodiment of the present invention that is performed in the system for an interventional procedure shown in FIG. 1.

FIG. 5 is an operational flowchart showing the procedure process of the method for an interventional procedure according to the embodiment of the present invention that is performed in the system for an interventional procedure shown in FIG. 1.

The steps of FIG. 5 are supported by a procedure software part, and may be loaded and executed by a processor of a computing system located inside the mobile master console 110 or connected to the mobile master console 110. In particular, steps S560 and S580 may be performed by an image processing apparatus of a computing system located inside the mobile master console 110 or connected to the mobile master console 110.

Referring to FIG. 5, surgical plan data is loaded into the mobile master console 110 by the procedure software at step S540.

Figure 6:
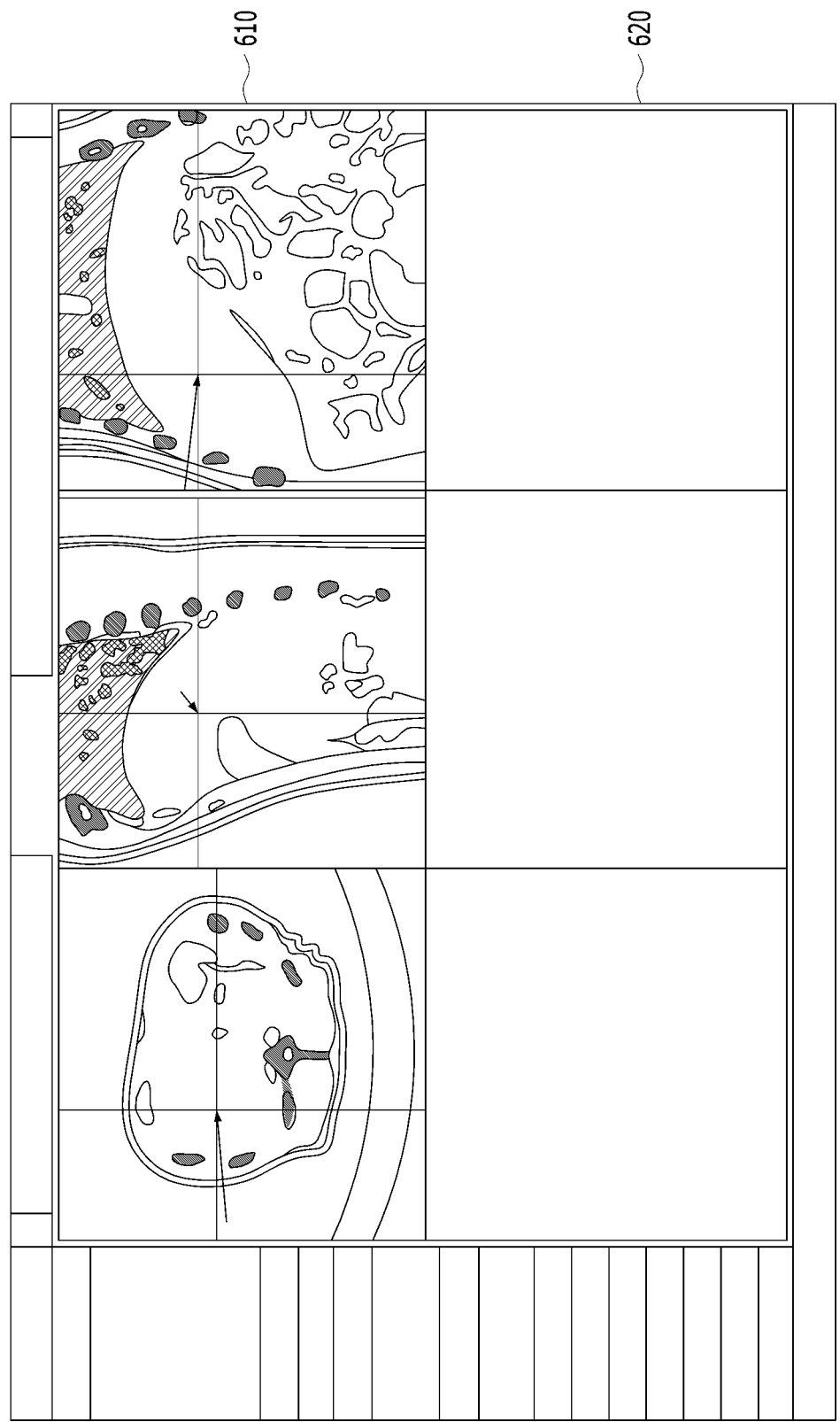
FIG. 6 is a view showing an example of the step of loading surgical plan data in the procedure process of the method for an interventional procedure shown in FIG. 5.

FIG. 6 is a view showing an example of step S540 of loading surgical plan data in the procedure process of the method for an interventional procedure shown in FIG. 5.

Referring to FIG. 6, the surgical plan data is loaded into and displayed in the first display area 610 of the screen of the SUI 120.

The second display area 620 of the screen of the SUI 120 remains blank until a subsequent action is performed.

Referring to back FIG. 5, pre-op CT images may be loaded into the mobile master console 110 by the procedure software at step S550.

The pre-op CT images are images that are acquired before surgery at a surgical site. Since the pre-op CT images are acquired at the surgery site, they are very similar to the images acquired in real time during surgery in terms of the posture and position of a patient, and thus they are relatively advantageous to contrast with real-time images.

Figure 7:
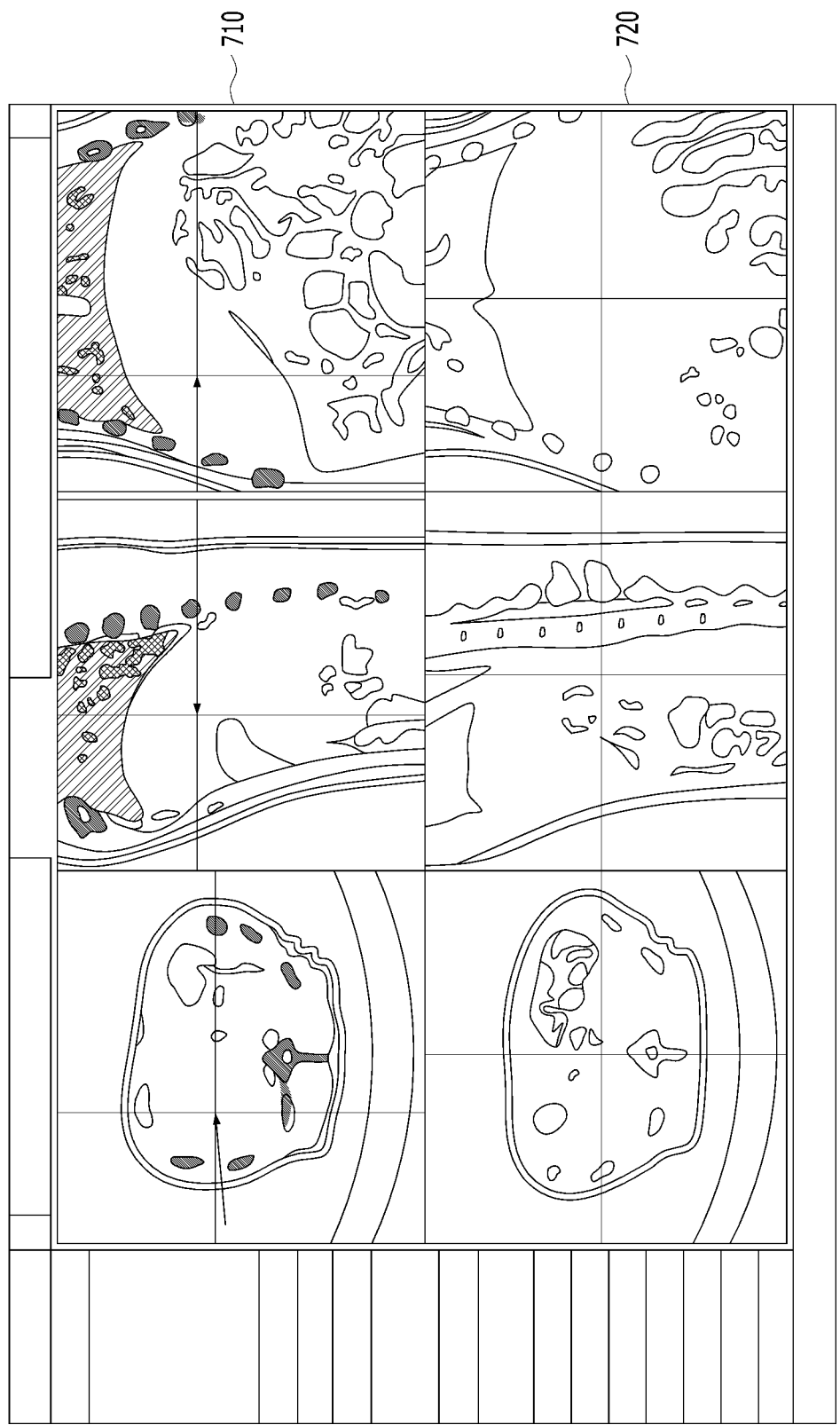
FIG. 7 is a view showing an example of the step of loading and displaying pre-op images in the procedure process of the method for an interventional procedure shown in FIG. 5.

FIG. 7 is a view showing an example of step S550 of loading and displaying pre-op images in the procedure process of the method for an interventional procedure shown in FIG. 5.

Referring to FIG. 7, in a state in which surgical plan data is loaded onto and displayed in the first display area 710 of the screen of the SUI 120, pre-op CT images are loaded onto and displayed in the second display area 720.

The surgical plan data is in the state of being mapped based on the plan CT images. There is a significant difference between the time at which the pre-op CT images are acquired and the time at which the plan CT images are acquired, and the position and posture of the patient are changed. Accordingly, to transfer the surgical plan data, set based on the plan CT images, to the pre-op CT images, it is necessary to register the pre-op CT images and the plan CT images.

Referring back to FIG. 5, the surgical plan data is transferred to the pre-op CT images by the procedure software at step S560. This step may be performed by an image processing device located inside the mobile master console 110 or connected to the mobile master console 110, and may be implemented in such a manner that the image processing device loads and executes the procedure software.

Figure 8:
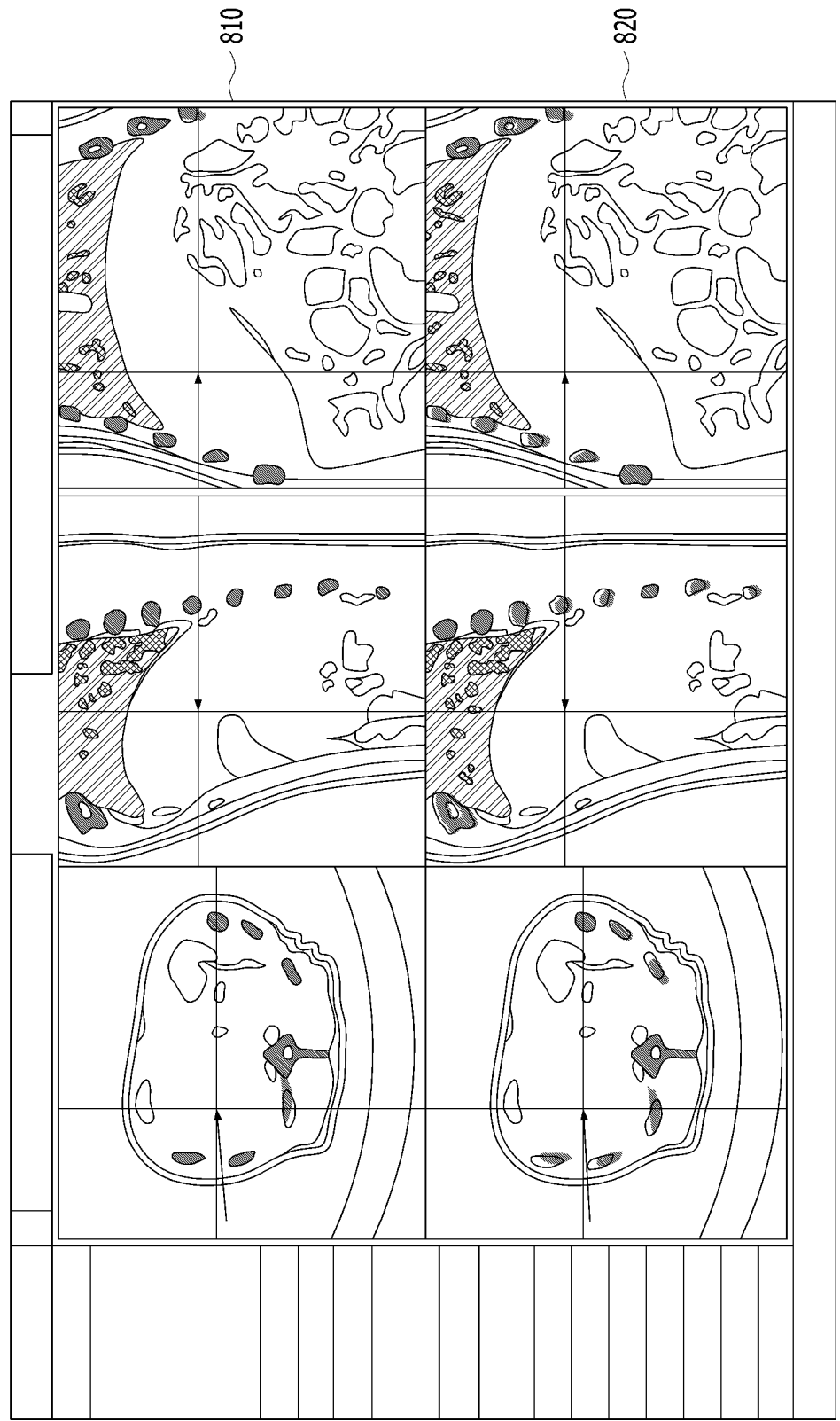
FIG. 8 is a view showing the step of transferring surgical plan data to pre-op images and displaying the surgical plan data transferred to the pre-op images in the procedure process of the method for an interventional procedure shown in FIG. 5.

FIG. 8 is a view showing the step of transferring surgical plan data to pre-op images and displaying the surgical plan data transferred to the pre-op images in the procedure process of the method for an interventional procedure shown in FIG. 5.

Referring to FIG. 8, in a state in which the surgical plan data is loaded and displayed in the first display area 810 of the screen of the SUI 120 and the pre-op CT images are loaded into and displayed in the second display area 820, the surgical plan data in the first display area 810 is transferred to the pre-op CT images in the second display area 820 and then displayed.

The procedure software that is executed in the image processing device registers the pre-op CT images and the plan CT images. In this case, the procedure software executed in the image processing device divides first and second regions in the pre-op CT images. Second anatomical structures are identified by performing image registration on the first region, and third anatomical structures corresponding to the first anatomical structures segmented in the plan CT images are registered for the second region.

As described above, since plan CT images are generally taken using a relatively high dose, they may have a high resolution. In addition, since a scan range centered on the location of a lesion is wide, it may be possible to accurately segment areas based on plan CT images and to set up a precise surgical plan.

Since the pre-op CT images acquired immediately before surgery at the surgical site are taken using a lower dose than general diagnostic CT images, the resolution thereof is considerably low, and a scan range centering on the location of a lesion is narrow. Accordingly, to perform a robotic procedure even based on low-resolution images, it is necessary to transfer accurate segmentation information and a precise procedure plan based on the plan CT images to low-resolution pre-op CT images.

Although the plan CT images and the pre-op CT images are medical images of the same patient, the posture, position, or breathing level of the patient vary. Accordingly, it takes a lot of time and resources to register the plan CT images and the pre-op CT images. The difference in the breathing level of the patient (the difference between the case of exhaling and the case of inhaling) causes differences in the relative positions or sizes of the organs of the patient, so it is one of the factors that require a lot of time and resources in image registration. However, since the time taken from the acquisition of the pre-op CT images to the start of surgery at a surgery site is not long, the registration between the pre-op CT images and the plan CT images needs to be performed rapidly, and, at the same time, the exact location of a procedure target area and a target point and segmentation from surrounding organs also need to be performed.

The system for an interventional procedure using medical images according to the present invention does not perform registration on the first area, which is a partial area of the pre-op CT images, but rapidly segments second anatomical structures in the first area, thereby distinguishing between main anatomical structures requiring registration, i.e., the first anatomical structures and the third anatomical structures corresponding thereto, and the second anatomical structures. Additionally, the time and resources required for the image registration process may be reduced by efficiently limiting image registration targets.

One of the criteria for distinguishing between the first and second areas in the pre-op images is the correlation with the surgical plan, and/or the intervention trajectories. The anatomical structures on the surgical plan or intervention trajectories are registered with the first anatomical structures in the plan CT images so that the locations of the former anatomical structures are identified, and anatomical structures having a low correlation with the surgical plan or intervention trajectories are segmented by image segmentation instead of being registered with the first anatomical structures in the plan CT images and may be recognized as the second anatomical structures distinguished from the first anatomical structures or third anatomical structures.

Another of the criteria for distinguishing between the first and second areas in the pre-op images is the use of the characteristics of the second anatomical structures and the third anatomical structures in the pre-op CT images. For example, since bones, skin, or the like, the segmentation of which in the CT images does not take a long time, have a relatively large area or volume and a segmentation time shorter than a registration time, they may be classified as the first area, and may be segmented into second anatomical structures by image segmentation. The lung, the airways, the vessels, lesions, or intervention trajectories, which are organs the segmentation of which takes a long time and the image conversion of which through registration takes a short time, may be classified as the second area, and may be recognized as the third anatomical structures by image registration.

The registration between the first anatomical structures and the third anatomical structures may be performed using non-rigid registration that is highly precise and requires a lot of time and resources, or rigid registration that sacrifices precision but requires less time and fewer resources. Rigid registration and non-rigid matching may be selectively combined based on available time, available resources, and computing power.

The segmentation of the second anatomical structures and the registration between the first anatomical structures and the third anatomical structures may be performed individually or may operate in a complementary manner. When the second anatomical structures derived as a result of the segmentation are present on the intervention trajectories as a result of the segmentation of the second anatomical structures and the registration between the first anatomical structures and the third anatomical structures that are performed individually, registration or segmentation may be performed again.

Referring back to FIG. 5, intra-op CT images are tracked by the procedure software and displayed through the SUI 120 at step S570.

Figure 9:
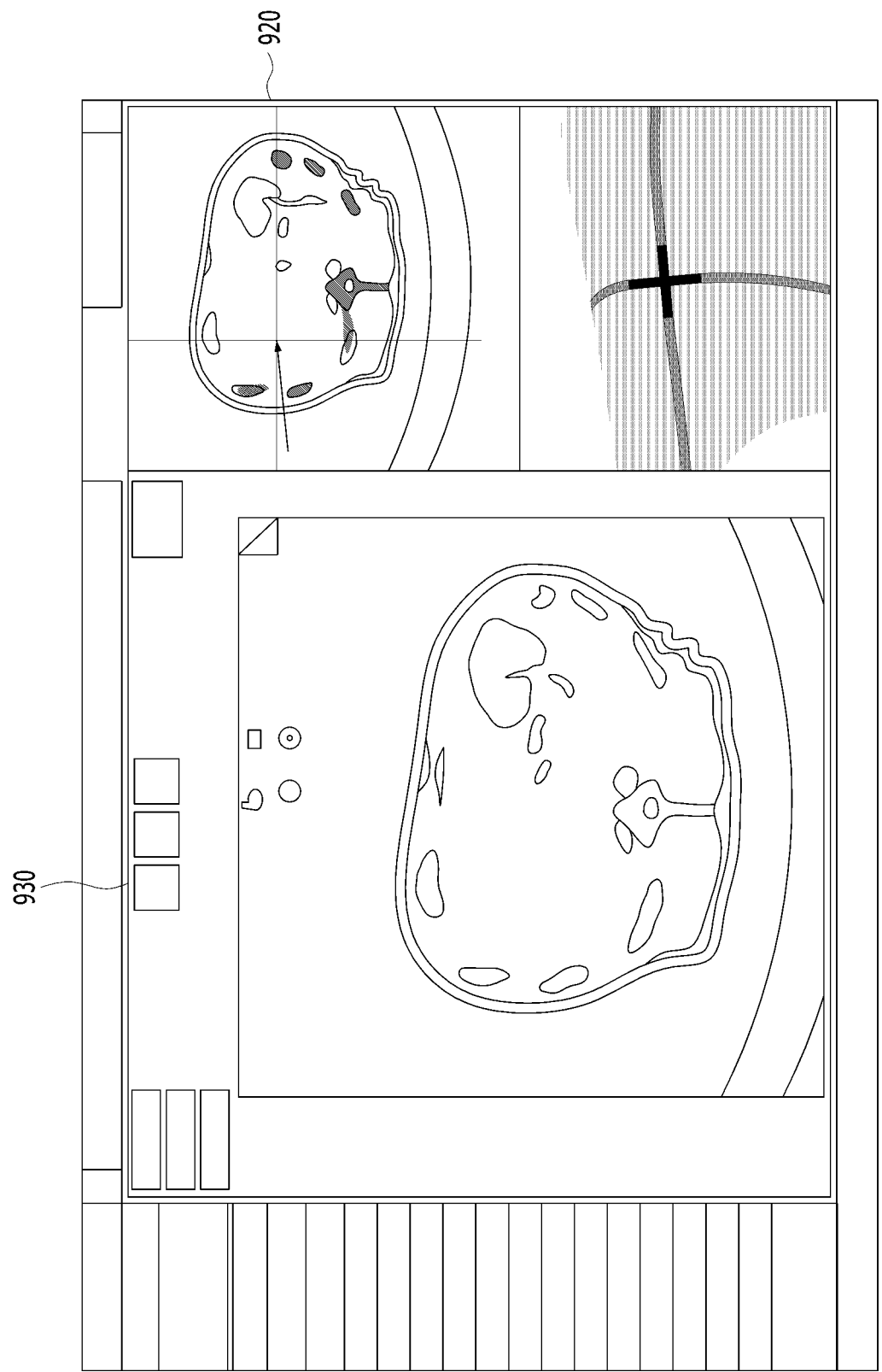
FIG. 9 is a view showing the step of displaying intra-op images (fluoroscopy images or fluoro images) in the procedure process of the method for an interventional procedure shown in FIG. 5.

FIG. 9 is a view showing the step of displaying intra-op images (fluoroscopy images or fluoro images) in the procedure process of the method for an interventional procedure shown in FIG. 5.

Referring to FIG. 9, in a state in which the pre-op CT images to which the surgical plan is transferred are displayed in the second display area 920 of the screen of the SUI 120, real-time intra-op images (fluoro CT images) are displayed in the third display area 930 of the screen.

Referring back to FIG. 5, the data of the pre-op CT images is transferred to the intra-op images by the procedure software loaded into and executed on the image processing device at step S580.

An intra-op procedure based on the intra-op images is performed by the procedure software loaded into and executed on the image processing device at step S590.

At step S590, information about intra-op images based on the intra-op procedure may be transferred to the pre-op images. In this case, the information about intra-op images transferred to the pre-op images may be the real-time current location and direction of a surgical tool. The real-time current location and direction of the surgical tool identified in the intra-op images may be mapped to 3D anatomical structure information and 3D spatial information in the pre-op CT images and compared with the surgical plan.

The pre-op images and the intra-op images may be registered by the procedure software that is executed by the image processing device. The current location and direction of the surgical tool in the intra-op images may be compared with the intervention trajectories on the surgical plan identified in the pre-op images. Whether the current location and the direction of the surgical tool deviate from the intervention trajectories on the surgical plan may be determined by the procedure software that is executed by the image processing device. Additionally, whether the surgical tool in the intra-op images invades or is likely to invade an anatomical structure that should not be invaded, i.e., an anatomical structure identified in the pre-op images, is determined by the procedure software that is executed by the image processing device.

As described above, in the case of performing registration using only a local model as in Korean Patent No. 10-1954868 entitled "Navigation System for Vascular Interventional Procedure and Virtual X-ray Image Generation Method" among the prior art, it is not possible to accurately identify and detect a case that a surgical tool at a surgical site invades an organ or deviates from trajectories, so that such accidents cannot be prevented in advance. Accordingly, information about surrounding anatomical structures as well as the local model needs to be utilized.

The system for an interventional procedure using medical images according to the present invention may utilize the anatomical structure information of the pre-op images having the highest similarity to the anatomical structures in the intra-op images, and may deal with association with insufficient information and surgical plan data attributable to low resolution by means of registration and association with the plan images having high resolution.

The system for an interventional procedure using medical images according to the present invention may register the intra-op images acquired in real time with the pre-op images including 3D anatomical information and 3D spatial information, thereby enabling the current location and direction of the surgical tool acquired in real time to be compared with the 3D anatomical information and the 3D spatial information without the loss of 3D information. Accordingly, the system for an interventional procedure using medical images according to the present invention may effectively determine whether the current location and direction of the surgical tool deviate from the surgical plan or the recommended intervention trajectories or whether the surgical tool is invading another organ or is likely to invade another organ in the future.

Even when the surgical plan and the plan image are not present, a system for an interventional procedure using medical images according to another embodiment of the present invention may utilize the anatomical structure information of the pre-op images, may acquire accurate information about the relationship between the anatomical structures in the intra-op images and the current location and direction of the surgical tool, and may improve the safety of an interventional procedure.

By the procedure software loaded into and executed on the image processing device, a fourth anatomical structure in the pre-op images may be identified by performing image segmentation on the pre-op images, and the fifth anatomical structure identified in the intra-op images may be registered with the fourth anatomical structure in the pre-op images.

By the procedure software loaded into and executed on the image processing device, whether the surgical tool in the intra-op images invades the anatomical structures identified in the pre-op images may be determined based on the current location and direction of the surgical tool in the real-time intra-op images.

The registration between the intra-op images and the pre-op images needs to be performed more rapidly. Since the intra-op images are real-time images, the available time and resources required for registration with the pre-op images are less and fewer. Since the intra-op images also use a low dose to reduce the possibility of the exposure of a patient to radiation, it is not easy to segment the anatomical structures in the intra-op images due to the low resolution.

Since the pre-op images have higher resolution and 3D spatial and structural information compared to the real-time intra-op images, more information is included in the pre-op images. In most of the prior art, to display information on the real-time intra-op images displayed on the SUI 120, the information of the pre-op images may be projected onto the real-time intra-op images, or a virtual 2D plane may be set and the information of the pre-op images may be projected onto the 2D plane. In the above prior art, the 3D spatial and structural information of the pre-op images is lost, and thus it is difficult for a surgeon to become aware of an exact location and 3D spatial and structural information. In the system for an interventional procedure using medical images according to the present invention, step S580 of transferring the information of the pre-op images to the SUI 120 may be included. However, during surgery, the information of the real-time intra-op images is transferred to the 3D pre-op images, and the information of the real-time intra-op images may be mapped to the 3D spatial and structural information in the 3D pre-op images and identified. The visualization of 3D pre-op images using a 3D technique is a separate issue. In the present invention, as to the 3D spatial and locational information that is most difficult for an surgeon to determine in a medical image guide-based interventional procedure, whether the real-time current location and direction of the surgical tool moves along the correct intervention trajectories may be determined through the identification of a location and identification based on the segmentation of anatomical structures in the pre-op images and then guidance may be performed through various techniques such as haptics.

Furthermore, in the above-described manner, when a treatment plan and plan CT images are present, the image guidance of an interventional procedure with high precision may be performed by the integrated software installed on the mobile master console 110. Even when plan CT images and a treatment plan are not present due to an urgent situation or the like, it may be possible to verify the current location and direction of the surgical tool through comparison with 3D spatial and structural information.

The system for an interventional procedure using medical images according to the present invention may provide the accurate analysis of 3D space and anatomical structure information using only medical images, and thus the safety, convenience, and accuracy of interventional procedure image guidance may be improved regardless of the presence of a treatment plan and plan CT images.

The system for an interventional procedure using medical images according to the present invention may improve the safety, convenience, and accuracy of interventional procedure image guidance without using a navigation system (referring to a system that constructs a space in which a location can be tracked in a real world space by receiving information from sensors attached to a patient and a device) that is used in the prior art.

The system for an interventional procedure using medical images according to the present invention does not require an additional location tracker used in the prior art, and may improve the safety, convenience, and accuracy of interventional procedure image guidance based on registration between images using only imaging equipment.

The system for an interventional procedure using medical images according to the present invention may generate a converted surgical plan and anatomical structure area rather than generating a virtual X-ray image using the results of registration.

The system for an interventional procedure using medical images according to the present invention performs registration on a 3D image rather than projecting a 3D image onto a 2D plane, and thus there is no loss of dimensional information.

The system for an interventional procedure using medical images according to the present invention may generate modified template images having different breathing levels for the segmented anatomical structures in the pre-op images. A first template image having a breathing level identical (closest) to that of the anatomical structures of the intra-op images may be searched for among a plurality of template images generated based on the segmented anatomical structures in the pre-op images. The anatomical structures of the intra-op images may be rapidly registered with the segmented anatomical structures in the pre-op images by reflecting the relationship between the first template image and the segmented anatomical structures in the pre-op images. Via the above-described modified example, the system and method for an interventional procedure using medical images according to the present invention may robustly determine the current location and direction of a surgical tool in the intra-op images even in an environment in which it is difficult to install a navigation system or a sensor or an environment in which it is difficult to acquire high-resolution intra-op images. In particular, the system and method for an interventional procedure using medical images according to the present invention may determine the current location and direction of a surgical tool in the 3D anatomical structures using the 3D anatomical structure information of the pre-op images. Whether the surgical tool is currently moving along the intervention trajectories, whether the surgical tool moves out of the intervention trajectories or is likely to invade another organ, or whether the surgical tool has already invaded another organ may be determined using the 3D anatomical structure information determined based on the segmentation of the pre-op images.

When breathing levels are pre-tuned and almost matched in the registration between the pre-op images and the plan images or between the pre-op images and the intra-op images, image registration is relatively easy. Accordingly, when the proportion of rigid body registration is large and breathing levels are not tuned in advance, the proportion of non-rigid registration may be large. In this case, when the breathing levels are not turned to each other, the time and resources required for image registration may be reduced through registration with a template image in which a breathing level has been tuned using a modified template of the breathing level.

Figure 10:
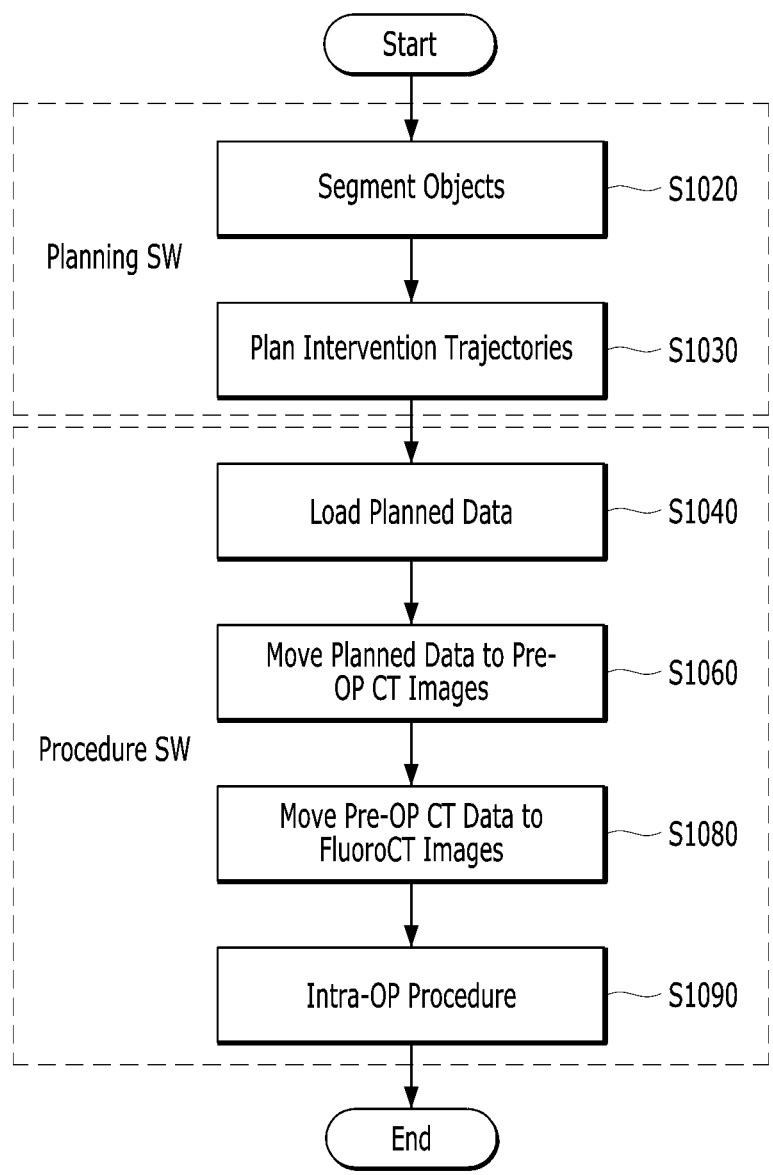
FIG. 10 is an operational flowchart showing a workflow that is performed by software, into which software for performing a planning process and software for performing a procedure process are integrated, in a method for an interventional procedure according to an embodiment of the present invention that is performed in the system for an interventional procedure shown in FIG. 1.

FIG. 10 is an operational flowchart showing a workflow that is performed by software, into which software for performing a planning process and software for performing a procedure process are integrated, in a method for an interventional procedure according to an embodiment of the present invention that is performed in the system for an interventional procedure shown in FIG. 1.

Referring to FIG. 10, the planning software module segments and identifies objects, i.e., anatomical structures, in plan images at step S1020.

At step S1030, the planning software module sets up a surgical plan, including the intervention trajectories of a surgical tool, based on the plan images.

The planning software module maps the surgical plans and the intervention trajectories into the segmented anatomical structures and stores the surgical plans and the intervention trajectories mapped into the segmented anatomical structures.

At step S1040, the procedure software module loads planned data.

At step S1060, the procedure software module transfers the planned data to the pre-op CT images.

At step S1080, the procedure software module transfers the data of the pre-op CT images to real-time intra-op images. In this case, in the pre-op CT images, a first region, which is an image segmentation target, and a second region, which is registered with the plan CT images, are distinguished from each other.

At step S1090, the procedure software module supports an interventional procedure while tracking the intra-op images. In this case, by the procedure software module, the 3D pre-op images and the real-time intra-op images are registered and the current location and trajectory of the surgical tool identified in the intra-op images are mapped into the anatomical structures in the pre-op images.

The method according to an embodiment of the present invention may be implemented in the form of program instructions, and may be then recorded in a computer-readable storage medium. The computer-readable storage medium may include program instructions, data files, and data structures solely or in combination. Program instructions recorded on the storage medium may have been specially designed and configured for the present invention, or may be known to or available to those who have ordinary knowledge in the field of computer software. Examples of the computer-readable storage medium include all types of hardware devices specially configured to record and execute program instructions, such as magnetic media, such as a hard disk, a floppy disk, and magnetic tape, optical media, such as compact disk (CD)-read only memory (ROM) and a digital versatile disk (DVD), magneto-optical media, such as a floptical disk, ROM, random access memory (RAM), and flash memory. Examples of the program instructions include machine code, such as code created by a compiler, and high-level language code executable by a computer using an interpreter. These hardware devices may be configured to operate as one or more software modules in order to perform the operation of the present invention, and the vice versa.

However, the present invention is not limited to the embodiments. Like reference symbols in the drawings designate like components. The lengths, heights, sizes, widths, etc. introduced in the embodiments and drawings of the present invention may be exaggerated to help to understand.

In accordance with the system for an interventional procedure using medical images according to the present invention, the workflow of planning and procedure processes may be provided via the integrated software and the integrated computing system.

In accordance with the system for an interventional procedure using medical images according to the present invention, the anatomical structure information of pre-op images having the highest similarity to the anatomical structures in intra-op images may be utilized and association with insufficient information and surgical plan data attributable to low resolution may be dealt with by means of registration and association with plan images having high resolution.

In accordance with the system for an interventional procedure using medical images according to the present invention, when a surgical plan and plan images are present, accurate information about the relationship between anatomical structures in intra-op images and the current location and direction of a surgical tool may be obtained based on high resolution.

In accordance with the system for an interventional procedure using medical images according to the present invention, even when a surgical plan and plan images are not present, the anatomical structure information of pre-op images may be utilized, accurate information about the relationship between anatomical structures in intra-op images and the current location and direction of a surgical tool based on high resolution may be obtained, and the safety of an interventional procedure may be improved.

In accordance with the system for an interventional procedure using medical images according to the present invention, the location and direction of a surgical tool in a 3D anatomical space may be determined using pre-op images in a pre-op planning stage or at a surgery site and intra-op images during surgery, so that the system for an interventional procedure does not require or may minimize additional location trackers, sensors attached to a patient, and/or a navigation system.

In accordance with the system for an interventional procedure using medical images according to the present invention, intra-op images acquired in real time may be registered with pre-op images including 3D anatomical information and 3D spatial information, thereby enabling the current location and direction of a surgical tool acquired in real time to be compared with the 3D anatomical information and the 3D spatial information without the loss of 3D information. Accordingly, according to the present invention, whether the current location and direction of the surgical tool deviates from a surgical plan or recommended intervention trajectories or whether the surgical tool is invading another organ or is likely to invade another organ in the future may be effectively determined.

Although the present invention has been described with reference to specific details such as the specific components, and the limited embodiments and drawings, these are provided merely to help a general understanding of the present invention, and the present invention is not limited thereto. Furthermore, those having ordinary skill in the technical field to which the present invention pertains may make various modifications and variations from the above detailed description.

Therefore, the spirit of the present invention should not be defined based only on the described embodiments, and not only the attached claims but also all equivalent to the claims should be construed as falling within the scope of the spirit of the present invention.

What is claimed is:

1. A system for an interventional procedure using medical images, the system comprising:
  a robot arm provided with a medical tool, and configured to operate such that the medical tool follows intervention trajectories;
  a master device configured to perform control so that the medical tool of the robot arm follows the intervention trajectories;
  an image processing device configured to:
    register plan images, in which a surgical plan including the intervention trajectories of the medical tool is set up, and preoperative (pre-op) images acquired at a surgical site before surgery so that the surgical plan is transferred to the pre-op images; and
    register the pre-op images and intraoperative (intra-op) images acquired at the surgical site during the surgery; and
  a user interface device configured to visualize a predicted arrival location of a tip of the medical tool for a target point when the robot arm operates according to the surgical plan by using the pre-op images, to which the surgical plan has been transferred, and the intra-op images in conjunction with the image processing device,
  wherein the image processing device is further configured to:
    distinguish a first area and a second area in the pre-op images before the registration of the pre-op images and the plan images, based on correlations of each of the first area and the second area with the surgical plan, wherein anatomical structures in the second area are on the intervention trajectories or a procedure target area of the surgical plan whereas anatomical structures in the first area are not;
    for the first area, identify second anatomical structures based on a segmentation-based identification by performing image segmentation instead of a registration-based identification; and
    for the second area, register third anatomical structures in the second area and first anatomical structures corresponding to the third anatomical structures in the plan images.

2. The system of claim 1, wherein the image processing device is further configured to distinguish the first and second areas in the pre-op images based on characteristics of the second and third anatomical structures in the pre-op images.

3. The system of claim 1, wherein the image processing device is further configured to:
  segment the first anatomical structures in the plan images; and
  map the intervention trajectories, included in the surgical plan, to the first anatomical structures.

4. The system of claim 1, wherein the image processing device is further configured to register the pre-op images and the intra-op images, thereby comparing a current location and direction of the surgical tool in the intra-op images with the intervention trajectories on the surgical plan identified in the pre-op images and determining whether the surgical tool in the intra-op images invades anatomical structures identified in the pre-op images.

5. A method for an interventional procedure using medical images, the method being performed by a computing system, the method comprising:
  acquiring or receiving plan images for a patient;
  performing image segmentation on the plan images, and identifying first anatomical structures in the plan images;
  setting up a surgical plan, including intervention trajectories of a surgical tool, based on the plan images;
  mapping the surgical plan to the first anatomical structures, and storing the surgical plan mapped to the first anatomical structures;
  loading the stored surgical plan;
  acquiring or receiving pre-op images acquired at a surgical site before surgery;
  transferring the surgical plan to the pre-op images by registering the plan images and the pre-op images;
  acquiring or receiving intra-op images acquired at the surgical site during the surgery; and
  mapping a current location and trajectory of the surgical tool, identified in the intra-op images, to anatomical structures in the pre-op images by registering the pre-op images and the intra-op images,
  wherein the transferring comprises:
    distinguishing a first area and a second area in the pre-op images before the registering the plan images and the pre-op images, based on correlations of each of the first area and the second area with the surgical plan, wherein anatomical structures in the second area are on the intervention trajectories or a procedure target area of the surgical plan whereas anatomical structures in the first area are not;
    identifying, for the first area, second anatomical structures based on a segmentation-based identification by performing image segmentation instead of a registration-based identification; and
    registering, for the second area, the first anatomical structures in the plan images and third anatomical structures in the second area corresponding to the first anatomical structures.

6. The method of claim 5, further comprising distinguishing the first and second areas in the pre-op images based on characteristics of the second and third anatomical structures in the pre-op images.

7. The method of claim 5, further comprising:
comparing a current location and direction of the surgical tool in the intra-op images with the intervention trajectories on the surgical plan identified in the pre-op images; and
determining whether the surgical tool in the intra-op images invades anatomical structures identified in the pre-op images.

\* \* \* \* \*